(12) United States Patent
Jia et al.

(10) Patent No.: US 11,710,571 B2
(45) Date of Patent: Jul. 25, 2023

(54) LONG SHORT-TERM MEMORY MODEL-BASED DISEASE PREDICTION METHOD AND APPARATUS, AND COMPUTER DEVICE

(71) Applicant: PING AN TECHNOLOGY (SHENZHEN) CO., LTD., Guangdong (CN)

(72) Inventors: Wenxiao Jia, Guangdong (CN); Kewei Tan, Guangdong (CN); Xiang Li, Guangdong (CN); Guotong Xie, Guangdong (CN)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 365 days.

(21) Appl. No.: 17/264,299

(22) PCT Filed: Aug. 30, 2019

(86) PCT No.: PCT/CN2019/103547
§ 371 (c)(1),
(2) Date: Jan. 29, 2021

(87) PCT Pub. No.: WO2020/220545
PCT Pub. Date: Nov. 5, 2020

(65) Prior Publication Data
US 2021/0296002 A1   Sep. 23, 2021

(30) Foreign Application Priority Data
Jun. 27, 2019   (CN) .......................... 201910570055.9

(51) Int. Cl.
*G16H 50/50*   (2018.01)
*G06N 3/0442*   (2023.01)
(Continued)

(52) U.S. Cl.
CPC ............. *G16H 50/50* (2018.01); *G06N 3/045* (2023.01); *G06N 3/0442* (2023.01); *G16H 50/20* (2018.01); *G16H 50/30* (2018.01)

(58) Field of Classification Search
CPC ......... G16H 10/00–80/00; G06N 3/00–99/007
See application file for complete search history.

(56) References Cited

U.S. PATENT DOCUMENTS

2018/0206797 A1 *   7/2018   Samiee ................ A61B 5/7275
2019/0057760 A1 *   2/2019   Schwartz ................. G06N 3/04
(Continued)

FOREIGN PATENT DOCUMENTS

| CN | 107145746 A | * | 9/2017 | |
| CN | 109599177 A | * | 4/2019 | ............ G16H 50/20 |
| CN | 109754852 A | * | 5/2019 | |

OTHER PUBLICATIONS

Ren et al., "A hybrid neural network model for predicting kidney disease in hypertension patients based on electronic health records," BMC Medical Informatics and Decision Making 2019, 19(Suppl 2):51; https://doi.org/10.1186/s12911-019-0765-4 (Year: 2019).*
(Continued)

*Primary Examiner* — Jonathon A. Szumny

(57) ABSTRACT

A long short-term memory (LSTM) model-based disease prediction method and apparatus, a computer device, and a storage medium are provided. The method includes: obtaining first medical data of a target object and second medical data of an associated object; inputting the first medical data and the second medical data into a first LSTM network in the LSTM model, to obtain a hidden state vector sequence in the first LSTM network; inputting the hidden state vector sequence into a second LSTM network for operation, to obtain a disease prediction result; selecting a predicted disease with an incidence rate higher than a preset threshold, and recording the predicted disease as a designated disease,
(Continued)

and obtaining, based on a preset disease association network, an associated disease directly connected to the designated disease; and outputting the disease prediction result and the associated disease, thereby improving the prediction accuracy.

20 Claims, 3 Drawing Sheets

(51) Int. Cl.
*G16H 50/20* (2018.01)
*G16H 50/30* (2018.01)
*G06N 3/045* (2023.01)

(56) References Cited

U.S. PATENT DOCUMENTS

| | | | |
|---|---|---|---|
| 2020/0000441 A1* | 1/2020 | Lafon | A61B 5/7282 |
| 2020/0265927 A1* | 8/2020 | Clark | G06N 3/084 |
| 2020/0293882 A1* | 9/2020 | Liu | G06N 3/044 |
| 2021/0068791 A1* | 3/2021 | Gebre | G06V 10/762 |
| 2021/0365736 A1* | 11/2021 | Kearney | A61B 1/000096 |

OTHER PUBLICATIONS

Lin et al., "Early Diagnosis and Prediction of Sepsis Shock by Combining Static and Dynamic Information using Convolutional-LSTM," 2018 IEEE International Conference on Healthcare Informatics. (Year: 2018).*

* cited by examiner

LONG SHORT-TERM MEMORY MODEL-BASED DISEASE PREDICTION METHOD AND APPARATUS, AND COMPUTER DEVICE

The present application claims priority to Chinese Patent Application No. 201910570055.9, filed with the China National Intellectual Property Administration on Jun. 27, 2019, and entitled "LONG SHORT-TERM MEMORY MODEL-BASED DISEASE PREDICTION METHOD AND APPARATUS, AND COMPUTER DEVICE", which is incorporated herein by reference in its entirety.

TECHNICAL FIELD

The present application relates to the computer field, and in particular, to a long short-term memory (LSTM) model-based disease prediction method and apparatus, a computer device, and a storage medium.

BACKGROUND

Disease risk prediction is implemented by combining artificial intelligence and medical science, and its core is to predict the probability of suffering from a certain disease within a time period in the future. Main calculation methods include classic regression analysis, conventional machine learning methods, and emerging deep learning methods. However, in real world, quality of medical data is poor, a data dimension is high, data is unbalanced, and a time sequence of medical data is discontinuous, leading to a high difficulty in accurately predicting risks of diseases. An existing disease risk prediction system requires a patient's physical examination data, but a physical examination process is time-consuming and laborious. Existing products can analyze a risk of a single disease only and cannot consider an association between diseases. In addition, existing products can only predict a risk of suffering from a disease within a time period in the future, and cannot consider time information of an input variable. Existing disease prediction considers only medical data of an object under test, and the prediction accuracy needs to be improved. Existing disease prediction products use only a single prediction model, and consequently the prediction accuracy is insufficient.

SUMMARY

Technical Problems

A main purpose of the present application is to provide a long short-term memory (LSTM) model-based disease prediction method and apparatus, a computer device, and a storage medium, so as to improve accuracy of disease prediction.

Technical Solutions

To achieve the foregoing purpose of invention, the present application provides an LSTM model-based disease prediction method. The method includes the following steps:

obtaining first medical data of a target object and second medical data of an associated object, where there is a blood relationship between the target object and the associated object; the first medical data includes a medication history, a disease history, and a surgery history; the second medical data includes a genetic disease treatment history;

inputting the first medical data and the second medical data into a first LSTM network in a trained LSTM model for operation, to obtain a hidden state vector sequence in the first LSTM network, where the LSTM model includes the first LSTM network for encoding and a second LSTM network for decoding;

inputting the hidden state vector sequence into the second LSTM network for operation, to obtain a disease prediction result, where the disease prediction result includes a predicted disease type and a corresponding incidence rate;

selecting a predicted disease with an incidence rate higher than a preset threshold from the disease prediction result, and recording the predicted disease as a designated disease, and obtaining, based on a preset disease association network, an associated disease directly connected to the designated disease, where network nodes of the association network are different types of diseases; and outputting the disease prediction result and the associated disease.

The present application provides an LSTM model-based disease prediction apparatus. The apparatus includes:

a medical data acquisition unit, configured to obtain first medical data of a target object and second medical data of an associated object, where there is a blood relationship between the target object and the associated object; the first medical data includes a medication history, a disease history, and a surgery history; the second medical data includes a genetic disease treatment history;

a hidden state vector sequence acquisition unit, configured to input the first medical data and the second medical data into a first LSTM network in a trained LSTM model for operation, to obtain a hidden state vector sequence in the first LSTM network, where the LSTM model includes the first LSTM network for encoding and a second LSTM network for decoding;

a disease prediction result acquisition unit, configured to input the hidden state vector sequence into the second LSTM network for operation, to obtain a disease prediction result, where the disease prediction result includes a predicted disease type and a corresponding incidence rate;

an associated disease acquisition unit, configured to select a predicted disease with an incidence rate higher than a preset threshold from the disease prediction result, and record the predicted disease as a designated disease, and obtain, based on a preset disease association network, an associated disease directly connected to the designated disease, where network nodes of the association network are different types of diseases; and an output unit, configured to output the disease prediction result and the associated disease.

The present application provides a computer device, including a memory and a processor, where the memory stores a computer program, and the processor executes the computer program to perform the steps of any one of the foregoing methods.

The present application provides a computer readable storage medium, where the computer readable storage medium stores a computer program, and the computer program is executed by a processor to perform the steps of any one of the foregoing methods.

Beneficial Effects

According to the LSTM model-based disease prediction method and apparatus, the computer device, and the storage medium in the present application, the first medical data of the target object and the second medical data of the associated object are obtained; the first medical data and the second medical data are input into the first LSTM network in the trained LSTM model for operation, to obtain the hidden state vector sequence in the first LSTM network; the hidden state vector sequence is input into the second LSTM network for operation, to obtain the disease prediction result; the predicted disease with an incidence rate higher than the preset threshold is selected from the disease prediction result, and recorded as the designated disease, and the associated disease directly connected to the designated disease is obtained based on the preset disease association network; and the disease prediction result and the associated disease are output. In this way, the prediction accuracy is improved.

The achievement of purposes, functional features, and advantages of the present application will be further described in combination with embodiments with reference to the accompanying drawings.

DESCRIPTION OF EMBODIMENTS

To make the purposes, the technical solutions, and the advantages of the present application clearer and more comprehensible, the following further describes the present application in detail with reference to the accompanying drawings and embodiments. It should be understood that the specific embodiments described herein are merely illustrative of the present application and are not intended to limit the present application.

Figure 1:
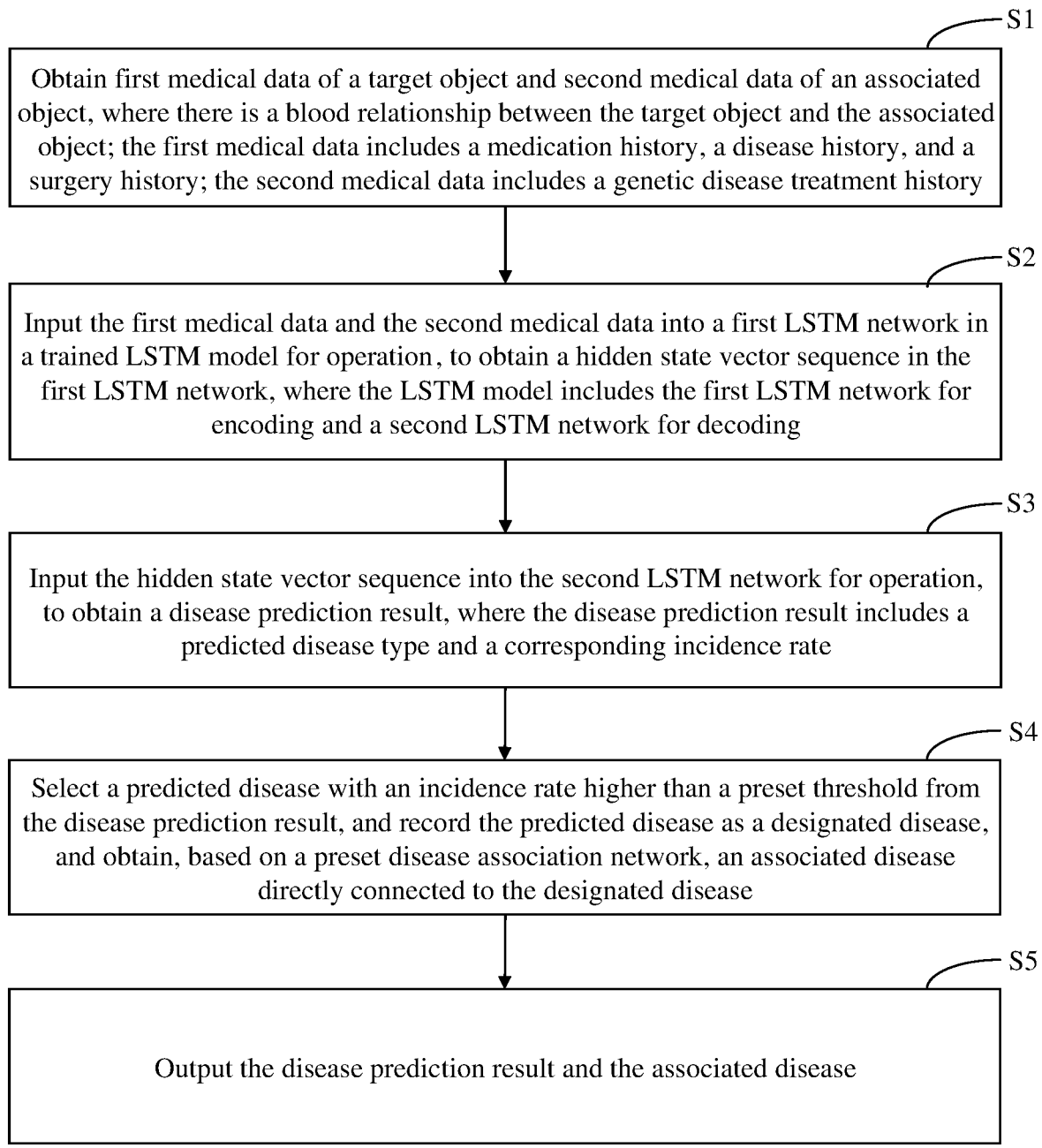
FIG. 1 is a schematic flowchart of an LSTM model-based disease prediction method according to an embodiment of the present application.

Referring to FIG. 1, an embodiment of the present application provides an LSTM model-based disease prediction method. The method includes the following steps:

S1: Obtain first medical data of a target object and second medical data of an associated object, where there is a blood relationship between the target object and the associated object; the first medical data includes a medication history, a disease history, and a surgery history; the second medical data includes a genetic disease treatment history.

S2: Input the first medical data and the second medical data into a first LSTM network in a trained LSTM model for operation, to obtain a hidden state vector sequence in the first LSTM network, where the LSTM model includes the first LSTM network for encoding and a second LSTM network for decoding.

S3: Input the hidden state vector sequence into the second LSTM network for operation, to obtain a disease prediction result, where the disease prediction result includes a predicted disease type and a corresponding incidence rate.

S4: Select a predicted disease with an incidence rate higher than a preset threshold from the disease prediction result, and record the predicted disease as a designated disease, and obtain, based on a preset disease association network, an associated disease directly connected to the designated disease, where network nodes of the association network are different types of diseases.

S5: Output the disease prediction result and the associated disease.

As described in step S1, the first medical data of the target object and the second medical data of the associated object are obtained, where there is a blood relationship between the target object and the associated object; the first medical data includes a medication history, a disease history, and a surgery history; the second medical data includes a genetic disease treatment history. The present application is used to predict a disease of the target object, and the second medical data of the associated object is used to assist in predicting the disease of the target object. The second medical data includes the genetic disease treatment history. Because a genetic disease is associated with blood, even if objects having a blood relationship do not show dominant characteristics of the genetic disease, they may have recessive physiological characteristics (latent disease). Therefore, the genetic disease treatment history of the associated object helps predict the disease of the target object. The first medical data includes a medication history, a disease history, and a surgery history. Because the medication history, the disease history, and the surgery history have impact on the human body, they can be used as a basis for disease prediction. For example, for patients who have used pioglitazone, captopril, and nitrendipine as historical medications for the treatment of diabetes, hypertension, and atrial fibrillation, the patients may be at risk of myocardial infarction, coronary heart disease, and stroke in the future. A conventional technology uses only a one-to-one analysis policy, that is, considers only the medical data of the target object to predict a future disease of the target object. The present application further uses the second medical data of the associated object as data for the prediction purpose, so as to increase the prediction accuracy. In addition, the conventional technology only models a single disease, and only a single disease can be predicted. In the present application, multiple diseases in different time periods can be predicted. The medical data in the present application not only includes the first medical data of the target object, but also considers the second medical data of the associated object, making the prediction more accurate and overcoming the shortcomings of the target object's false reporting of a medical history and concealment of a family medical history (to be specific, even if the genetic disease in the target object is recessive, it still exists at the genetic level and may be dominant in the future, and may also have impact on body functions and other diseases; therefore, the second medical data of the associated object is used to know the data such as the genetic disease of the target object, thereby improving the accuracy of disease prediction).

As described in step S2, the first medical data and the second medical data are input into the first LSTM network in the trained LSTM model for operation, to obtain the hidden state vector sequence in the first LSTM network, where the LSTM model includes the first LSTM network for encoding and the second LSTM network for decoding. The LSTM model is a model that uses an LSTM network. The LSTM network is a time recurrent neural network, which is suitable for processing and predicting important events with relatively long intervals and delays in a time sequence. Unlike an ordinary recurrent neural network, the LSTM network includes a "processor" for determining whether information is useful. Only information that conforms to algorithm authentication is left, and unconformable information is forgotten through a forget gate, thereby solving the problem of long-term dependence. The LSTM model used in the present application includes the first LSTM network for encoding and the second LSTM network for decoding, so as to implement temporal prediction of multiple diseases. In the present application, encoding refers to converting the input information into a vector sequence of a specified length, and decoding refers to converting the input vector sequence into a predicted vector sequence.

As described in step S3, the hidden state vector sequence is input into the second LSTM network for operation, to obtain the disease prediction result, where the disease prediction result includes the predicted disease type and the corresponding incidence rate. The second LSTM network can perform operation using any method, for example, using the following formulas:

$$\hat{s}_t = \tanh(W_c[c_i; s_t]), c_i = \sum_{j=1}^{n} \alpha_{ij} h_j, \alpha_{ij} = \frac{\exp(e_{ij})}{\sum_{k=1}^{n} \exp(e_{ik})},$$

$$e_{ij} = \text{score}(s_i, h_j), \text{ and } p(y_t | y < t, x) = \text{softmax}(W_s \hat{s}_t),$$

where $c_i$ represents the final hidden state vector $c_i$ in the first LSTM network; $a_{ij}$ represents a weighting parameter, and there are n time periods in total; $s_i$ represents the i-th hidden state vector in the second LSTM network; score($s_i$,$h_j$) represents a score calculated based on $s_i$ and $h_j$ using a preset score function; $W_C$ represents a weight value; p represents an output probability; $y_t$ represents an output of the second LSTM network corresponding to the t-th time period; and x represents an input (directly related to the first medical data and the second medical data).

As described in step S4, the predicted disease with an incidence rate higher than the preset threshold is selected from the disease prediction result, and recorded as the designated disease, and the associated disease directly connected to the designated disease is obtained based on the preset disease association network, where the network nodes of the association network are different types of diseases. The disease association network may be any association network, such as a knowledge graph network. The knowledge graph network is constructed, for example, by using the following method: A preset knowledge graph construction tool is used to identify initial entities from designated information collected in advance, where the designated information records at least the designated disease, and the initial entities include at least the designated disease; the initial entities are deduplicated to obtain final entities; a relationship between the final entities is extracted from the designated information to form a triplet, and the knowledge graph network is generated based on the triplet. In this way, prediction is further performed based on the LSTM model, further improving the prediction accuracy.

As described in step S5, the disease prediction result and the associated disease are output. The disease prediction result is the output result of the LSTM model, and the associated disease is the output result of the disease association network, so that the prediction accuracy is further improved by combining the LSTM model and the disease association network.

In an implementation, step S2 of inputting the first medical data and the second medical data into a first LSTM network in a trained LSTM model for operation, to obtain a hidden state vector sequence in the first LSTM network includes the following:

S201: Divide the first medical data into multiple data sequences based on preset time periods.

S202: Obtain a designated impact factor of the genetic disease in the second medical data on other diseases based on a preset correspondence between the genetic disease and impact factors of other diseases.

S203: Input the multiple data sequences and the designated impact factor into the first LSTM network in the trained LSTM model for operation, to obtain the hidden state vector sequence in the first LSTM network.

As described above, the hidden state vector sequence in the first LSTM network is obtained. The designated impact factor has the same value or dynamically varying values in different time periods (because a degree of impact of the genetic disease on other diseases changes over time). The first medical data is medical data in a time period, which is divided into multiple data sequences in different time periods. In addition, to accommodate the second medical data into the LSTM model, the present application reflects the second medical data as the designated impact factor, so that the multiple data sequences and the designated impact factor are jointly used as the input of the LSTM model. Specifically, a high-dimensional vector is generated for a single data sequence and a corresponding designated impact factor. Therefore, a high-dimensional vector sequence is generated for multiple data sequences and respective corresponding designated impact factors, and is used as a calculation basis in the trained LSTM model. Other diseases are diseases other than the genetic disease. The impact factor refers to data obtained by quantifying the impact of the genetic disease on other diseases, and is used for calculation in the LSTM network. The impact factor may exist in any form, for example, in the form of a separate vector.

In an implementation, step S203 of inputting the multiple data sequences and the designated impact factor into the first LSTM network in the trained LSTM model for operation, to obtain the hidden state vector sequence in the first LSTM network includes the following:

S2031: Obtain a hidden state vector $h_t$ in the first LSTM network according to the following formula: $h_t = \text{LSTM}_{enc}(x_t, h_{t-1})$, where t represents the t-th time period; $h_t$ represents a hidden state vector corresponding to the t-th time period; $h_{t-1}$ represents a hidden state vector corresponding to the (t−1)-th time period; $X_t$ represents input data in the t-th time period; and $\text{LSTM}_{enc}$ refers to an encoding operation using the first LSTM network, where $X_t$ includes first medical data corresponding to the t-th time period and a designated impact factor corresponding to the t-th time period.

S2032: Construct a hidden state vector sequence $h_1$, $h_2$, ..., $h_n$ by using the hidden state vectors corresponding to multiple preset time periods, where there are n time periods in total.

As described above, the multiple data sequences and the designated impact factor are input into the first LSTM network in the trained LSTM model for operation, to obtain the hidden state vector sequence in the first LSTM network. In the present application, the hidden state vector $h_t$ in the first LSTM network is obtained by using the following formula: $h_t = \text{LSTM}_{enc}(x_t, h_{t-1})$, and a hidden state vector sequence $h_1$, $h_2$, ..., $h_n$ is constructed by using the hidden state vectors corresponding to multiple preset time periods, where there are n time periods in total. On this basis, the first LSTM network encodes the multiple data sequences and the designated impact factor into a hidden state vector sequence, which serves as a decoding basis for the second LSTM network.

In an implementation, step S2032 of constructing a hidden state vector sequence $h_1$, $h_2$, ..., $h_n$ by using the hidden state vectors corresponding to multiple preset time periods, where there are n time periods in total, includes the following:

S20321: Obtain the final hidden state vector $c_i$ in the first LSTM network according to the following formulas:

$$c_i = \sum_{j=1}^{n} \alpha_{ij} h_j, \; \alpha_{ij} = \frac{\exp(e_{ij})}{\sum_{k=1}^{n} \exp(e_{ik})}, \text{ and } e_{ij} = \text{score}(s_i, h_j),$$

where $a_{ij}$ represents a weighting parameter, and there are n time periods in total; $s_i$ represents the i-th hidden state vector in the second LSTM network; score($s_i,h_j$) represents a score calculated based on $s_i$ and $h_j$ using a preset score function.

S20322: Construct a hidden state vector sequence $c_1$, $c_2, \ldots, c_n$ by using the final hidden state vectors corresponding to multiple preset time periods.

As described above, the hidden state vector sequence $h_1$, $h_2, \ldots, h_n$ is constructed by using the hidden state vectors corresponding to multiple preset time periods. In the present application, the final hidden state vector $c_i$ in the first LSTM network is obtained according to the following formulas:

$$c_i = \sum_{j=1}^{n} \alpha_{ij} h_j, \; \alpha_{ij} = \frac{\exp(e_{ij})}{\sum_{k=1}^{n} \exp(e_{ik})}, \text{ and } e_{ij} = \text{score}(s_i, h_j),$$

that is, an attention mechanism is introduced to automatically capture information important to the outcome. In this way, the final hidden state vector sequence serves as a decoding basis for the second LSTM network. Because the attention mechanism is used, weight allocation is more accurate, helping improve the prediction accuracy.

In an implementation, step S3 of inputting the hidden state vector sequence into the second LSTM network for operation, to obtain a disease prediction result, where the disease prediction result includes a predicted disease type and a corresponding incidence rate, includes the following:

S301: Input the hidden state vector sequence into the second LSTM network for operation, to obtain a high-dimensional vector sequence that is output by the second LSTM network.

S302: Interpret the high-dimensional vector sequence based on a preset correspondence between a component vector and a meaning of the prediction result, so as to obtain disease prediction results in different time periods in the future, where the disease prediction result includes the predicted disease type and the corresponding incidence rate.

As described above, the hidden state vector sequence is input into the second LSTM network for operation, to obtain the disease prediction result. The output of the second LSTM network is a high-dimensional vector sequence. The high-dimensional vector sequence represents the prediction results in different time periods, and the component vector of the high-dimensional vector represents the predicted disease type and the corresponding incidence rate. Predicted disease types and corresponding incidence rates in different time periods in the future can be obtained based on the preset correspondence between a component vector and a meaning of the prediction result.

In an implementation, after step S3 of inputting the hidden state vector sequence into the second LSTM network for operation, to obtain a disease prediction result, where the disease prediction result includes a predicted disease type and a corresponding incidence rate, the method includes the following steps:

S311: Receive multiple input improvement factor groups, and input the improvement factor groups, the first medical data, and the second medical data into the trained LSTM model for calculation, where the improvement factor groups include carrying out of medication or surgery at designated time points.

S312: Obtain multiple groups of improved disease prediction results respectively corresponding to the multiple improvement factor groups output by the LSTM model, where the improved disease prediction results include predicted disease types and corresponding incidence rates.

S313: Select a final improved disease prediction result from the multiple groups of improved disease prediction results based on a preset selection rule, and generate a recommended treatment plan, where the recommended treatment plan is accompanied by an improvement factor group corresponding to the final improved disease prediction result.

As described above, the recommended treatment plan is generated. Because the input in the present application is medical data that includes a medication history and a surgery history, hypothetical medication or surgery can also be accepted. Thus, the LSTM model in the present application can simulate the curative effect of the treatment plan. Therefore, multiple input improvement factor groups are received, and the improvement factor groups, the first medical data, and the second medical data are input into the trained LSTM model for calculation, where the improvement factor groups include carrying out of medication or surgery at designated time points; multiple groups of improved disease prediction results respectively corresponding to the multiple improvement factor groups output by the LSTM model are obtained, where the improved disease prediction results include predicted disease types and corresponding incidence rates; the final improved disease prediction result is selected from the multiple groups of improved disease prediction results based on a preset selection rule, and a recommended treatment plan is generated, where the recommended treatment plan is accompanied by the improvement factor group corresponding to the final improved disease prediction result. For example, the preset selection rule is that the predicted disease type is the least, or the incidence rate of the predicted disease type is less than a preset threshold.

In an implementation, the disease association network is a knowledge graph network; before step S4 of obtaining, based on the preset disease association network, the associated disease directly connected to the designated disease, where the network nodes of the association network are different types of diseases, the method includes the following steps:

S321: Use a preset knowledge graph construction tool to identify initial entities from designated information collected in advance, where the designated information records at least the designated disease, and the initial entities include at least the designated disease.

S322: Deduplicate the initial entities to obtain final entities.

S323: Extract a relationship between the final entities from the designated information to form a triplet, and generate the knowledge graph network based on the triplet.

As described above, the knowledge graph that includes the designated members is constructed. The preset knowledge graph construction tool may be any tool, such as the existing SPSS, Ucinet NetDraw, and VOSviewer. Because the above tools are existing knowledge graph construction tools, they are not described. The designated information records disease information, based on which an association relationship between diseases can be known. The entity is a knowledge node in the knowledge graph, and the initial entity is a knowledge node that has not been deduplicated. For example, the process of identifying the initial entity is performing word segmentation on the designated information to obtain a word sequence consisting of multiple words, and inputting the word sequence into a preset sentence structure model to obtain the initial entity from the word sequence. Then, the initial entity is deduplicated to obtain the final entity. For example, the deduplication process is performing synonym judgment on all initial entities, and replacing the initial entities belonging to the same synonym group with a word in the synonym group. Then, a relationship between final entities is extracted from the designated information to form a triplet, and the knowledge graph that includes the designated members is generated based on the triplet. For example, the triplet refers to the relationship between two entities. For example, the method for extracting the relationship between the final entities from the designated information is inputting the designated information into a preset sentence structure to extract a vocabulary that expresses the relationship between multiple entities through the sentence structure. On this basis, a relationship between diseases is expressed in the form of a knowledge graph network, and the disease type serves as a knowledge node in the knowledge graph. Further, the knowledge nodes of the knowledge graph may further include entities other than disease types.

According to the LSTM model-based disease prediction method in the present application, the first medical data of the target object and the second medical data of the associated object are obtained; the first medical data and the second medical data are input into the first LSTM network in the trained LSTM model for operation, to obtain the hidden state vector sequence in the first LSTM network; the hidden state vector sequence is input into the second LSTM network for operation, to obtain the disease prediction result; the predicted disease with an incidence rate higher than the preset threshold is selected from the disease prediction result, and recorded as the designated disease, and the associated disease directly connected to the designated disease is obtained based on the preset disease association network; and the disease prediction result and the associated disease are output. In this way, the prediction accuracy is improved.

Figure 2:
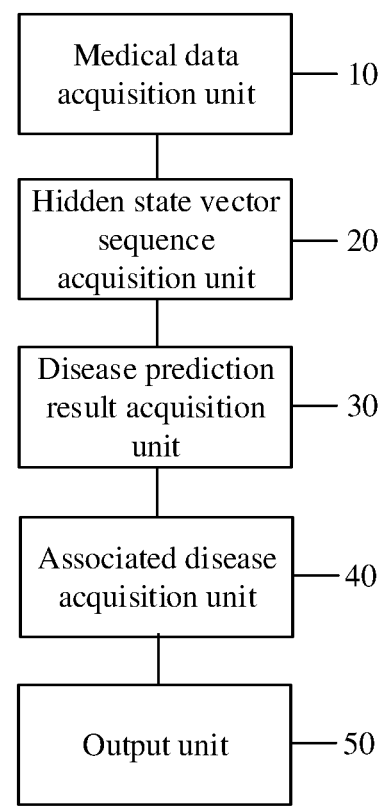
FIG. 2 is a schematic structural block diagram of an LSTM model-based disease prediction apparatus according to an embodiment of the present application.

Referring to FIG. 2, an embodiment of the present application provides an LSTM model-based disease prediction apparatus. The apparatus includes:

a medical data acquisition unit 10, configured to obtain first medical data of a target object and second medical data of an associated object, where there is a blood relationship between the target object and the associated object; the first medical data includes a medication history, a disease history, and a surgery history; the second medical data includes a genetic disease treatment history;

a hidden state vector sequence acquisition unit 20, configured to input the first medical data and the second medical data into a first LSTM network in a trained LSTM model for operation, to obtain a hidden state vector sequence in the first LSTM network, where the LSTM model includes the first LSTM network for encoding and a second LSTM network for decoding;

a disease prediction result acquisition unit 30, configured to input the hidden state vector sequence into the second LSTM network for operation, to obtain a disease prediction result, where the disease prediction result includes a predicted disease type and a corresponding incidence rate;

an associated disease acquisition unit 40, configured to select a predicted disease with an incidence rate higher than a preset threshold from the disease prediction result, and record the predicted disease as a designated disease, and obtain, based on a preset disease association network, an associated disease directly connected to the designated disease, where network nodes of the association network are different types of diseases; and an output unit 50, configured to output the disease prediction result and the associated disease.

The operations respectively performed by the foregoing units are in one-to-one correspondence to the steps of the LSTM model-based disease prediction method in the foregoing implementation respectively, and are not described herein again.

In an implementation, the hidden state vector sequence acquisition unit 20 includes:

a multiple data sequence acquisition subunit, configured to divide the first medical data into multiple data sequences based on preset time periods;

a designated impact factor acquisition subunit, configured to obtain a designated impact factor of the genetic disease in the second medical data on other diseases based on a preset correspondence between the genetic disease and impact factors of other diseases; and a hidden state vector sequence acquisition subunit, configured to input the multiple data sequences and the designated impact factor into the first LSTM network in the trained LSTM model for operation, to obtain the hidden state vector sequence in the first LSTM network.

The operations respectively performed by the foregoing subunits are in one-to-one correspondence to the steps of the LSTM model-based disease prediction method in the foregoing implementation respectively, and are not described herein again.

In an implementation, the hidden state vector sequence acquisition subunit includes:

a hidden state vector calculation module, configured to obtain a hidden state vector $h_t$ in the first LSTM network according to the following formula: $h_t = LSTM_{enc}(x_t, h_{t-1})$, where t represents the t-th time period; $h_t$ represents a hidden state vector corresponding to the t-th time period; $h_{t-1}$ represents a hidden state vector corresponding to the (t−1)-th time period; $X_t$ represents input data in the t-th time period; and $LSTM_{enc}$ refers to an encoding operation using the first LSTM network, where $X_t$ includes first medical data corresponding to the t-th time period and a designated impact factor corresponding to the t-th time period; and a hidden state vector sequence acquisition module, configured to construct a hidden state vector sequence $h_1, h_2, \ldots, h_n$ by using hidden state vectors corresponding to multiple preset time periods, where there are n time periods in total.

The operations respectively performed by the foregoing modules are in one-to-one correspondence to the steps of the LSTM model-based disease prediction method in the foregoing implementation respectively, and are not described herein again.

In an implementation, the hidden state vector sequence acquisition module includes:

a final hidden state vector acquisition submodule, configured to obtain the final hidden state vector $c_i$ in the first LSTM network according to the following formulas:

$$c_i = \sum_{j=1}^{n} \alpha_{ij} h_j, \quad \alpha_{ij} = \frac{\exp(e_{ij})}{\sum_{k=1}^{n} \exp(e_{ik})}, \quad \text{and} \quad e_{ij} = \text{score}(s_i, h_j),$$

where $a_{ij}$ represents a weighting parameter, and there are n time periods in total; $s_i$ represents the i-th hidden state vector in the second LSTM network; $\text{score}(s_i, h_j)$ represents a score calculated based on $s_i$ and $h_j$ using a preset score function; and a hidden state vector sequence acquisition submodule, configured to construct a hidden state vector sequence $c_1$, $c_2$, ..., $c_n$ by using final hidden state vectors corresponding to multiple preset time periods.

The operations respectively performed by the foregoing submodules are in one-to-one correspondence to the steps of the LSTM model-based disease prediction method in the foregoing implementation respectively, and are not described herein again.

In an implementation, the disease prediction result acquisition unit 30 includes:

a high-dimensional vector sequence acquisition subunit, configured to input the hidden state vector sequence into the second LSTM network for operation, to obtain a high-dimensional vector sequence that is output by the second LSTM network; and a disease prediction result acquisition subunit, configured to interpret the high-dimensional vector sequence based on a preset correspondence between a component vector and a meaning of the prediction result, so as to obtain disease prediction results in different time periods in the future, where the disease prediction result includes the predicted disease type and the corresponding incidence rate.

The operations respectively performed by the foregoing subunits are in one-to-one correspondence to the steps of the LSTM model-based disease prediction method in the foregoing implementation respectively, and are not described herein again.

In an implementation, the apparatus includes:

an improvement factor group receiving unit, configured to receive multiple input improvement factor groups, and input the improvement factor groups, the first medical data, and the second medical data into the trained LSTM model for calculation, where the improvement factor groups include carrying out of medication or surgery at designated time points;

an improved disease prediction result acquisition unit, configured to obtain multiple groups of improved disease prediction results respectively corresponding to the multiple improvement factor groups output by the LSTM model, where the improved disease prediction results include predicted disease types and corresponding incidence rates; and a recommended treatment plan generation unit, configured to select a final improved disease prediction result from the multiple groups of improved disease prediction results based on a preset selection rule, and generate a recommended treatment plan, where the recommended treatment plan is accompanied by the improvement factor group corresponding to the final improved disease prediction result.

The operations respectively performed by the foregoing units are in one-to-one correspondence to the steps of the LSTM model-based disease prediction method in the foregoing implementation respectively, and are not described herein again.

In an implementation, the disease association network is a knowledge graph network, and the apparatus includes:

an initial entity identification unit, configured to use a preset knowledge graph construction tool to identify initial entities from designated information collected in advance, where the designated information records at least the designated disease, and the initial entities include at least the designated disease;

a final entity acquisition unit, configured to deduplicate the initial entities to obtain final entities; and a knowledge graph network generation unit, configured to extract a relationship between the final entities from the designated information to form a triplet, and generate the knowledge graph network based on the triplet.

The operations respectively performed by the foregoing units are in one-to-one correspondence to the steps of the LSTM model-based disease prediction method in the foregoing implementation respectively, and are not described herein again.

According to the LSTM model-based disease prediction apparatus in the present application, the first medical data of the target object and the second medical data of the associated object are obtained; the first medical data and the second medical data are input into the first LSTM network in the trained LSTM model for operation, to obtain the hidden state vector sequence in the first LSTM network; the hidden state vector sequence is input into the second LSTM network for operation, to obtain the disease prediction result; the predicted disease with an incidence rate higher than the preset threshold is selected from the disease prediction result, and recorded as the designated disease, and the associated disease directly connected to the designated disease is obtained based on the preset disease association network; and the disease prediction result and the associated disease are output. In this way, the prediction accuracy is improved.

Figure 3:
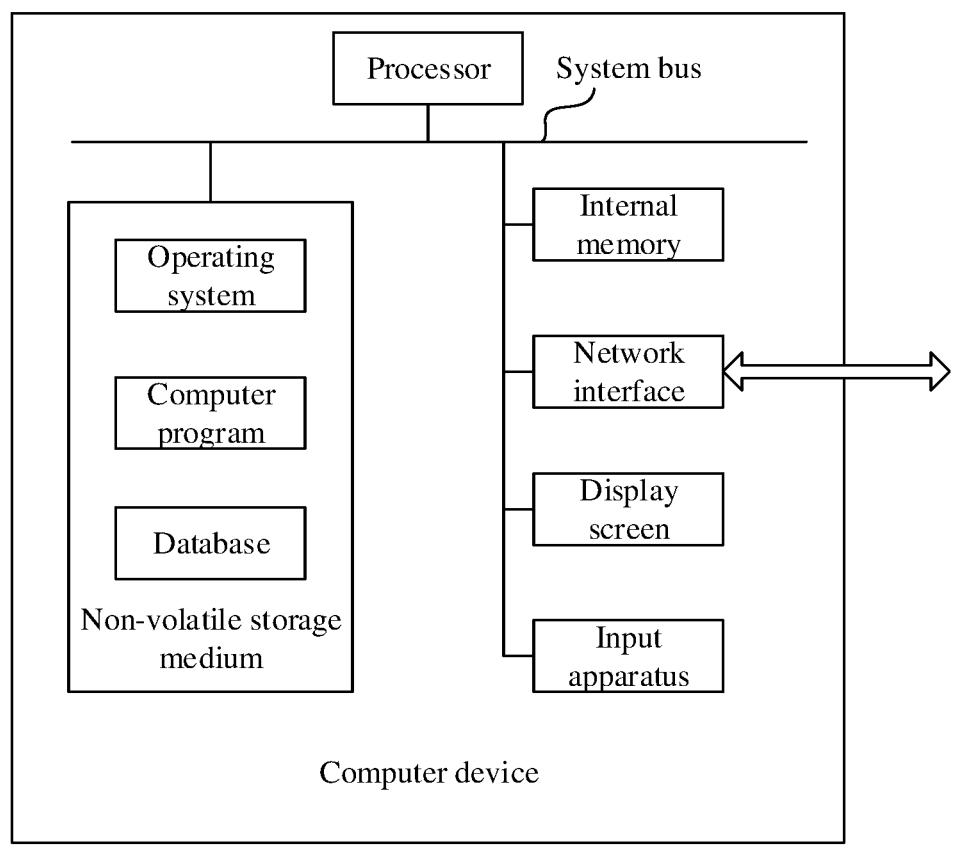
FIG. 3 is a schematic structural block diagram of a computer device according to an embodiment of the present application.

Referring to FIG. 3, an embodiment of the present application further provides a computer device. The computer device may be a server, and its internal structure may be shown in the figure. The computer device includes a processor, a memory, a network interface, and a database that are connected through a system bus. The processor of the computer device is configured to provide computing and control capabilities. The memory of the computer device includes a non-volatile storage medium and an internal memory. The non-volatile storage medium stores an operating system, a computer program, and a database. The internal memory provides an environment for the operations of the operating system and the computer program in the non-volatile storage medium. The database of the computer device is configured to store data used by the LSTM model-based disease prediction method. The network interface of the computer device is configured to communicate with an external terminal through a network connection. The computer program is executed by the processor to perform the LSTM model-based disease prediction method.

The processor performs the foregoing LSTM model-based disease prediction method, where the steps included in the method are in one-to-one correspondence to the steps of the LSTM model-based disease prediction method in the foregoing implementation respectively, and are not described herein again.

A person skilled in the art can understand that the structure shown in the figure is merely a block diagram of a partial structure related to the solution of the present application, and does not constitute a limitation on the computer device to which the solution of the present application is applied.

An embodiment of the present application further provides a computer readable storage medium, where the computer readable storage medium stores a computer program; the computer program is executed by a processor to perform an LSTM model-based disease prediction method; the steps included in the method are in one-to-one correspondence to the steps of the LSTM model-based disease prediction method in the foregoing implementation respectively, and are not described herein again.

A person of ordinary skill in the art may understand that all or some of the processes of the method in the embodiments may be implemented by a computer program instructing related hardware. The computer program may be stored in a non-volatile computer readable storage medium. When the computer program runs, the processes of the method in the embodiments are performed. Any reference to a memory, storage, a database, or other media provided by the present application and used in the embodiments may include a non-volatile memory and/or volatile memory. The non-volatile memory may include a read only memory (ROM), a programmable ROM (PROM), an electrically programmable ROM (EPROM), an electrically erasable programmable ROM (EEPROM), or a flash memory. The volatile memory may include a random access memory (RAM) or an external cache memory. By way of illustration and not limitation, the RAM is available in a variety of forms, such as a static RAM (SRAM), a dynamic RAM (DRAM), a synchronous DRAM (SDRAM), a double data rate SDRAM (DDR SDRAM), an enhanced SDRAM (ESDRAM), a synchlink DRAM (SLDRAM), a Rambus dynamic RAM (RDRAM), a direct Rambus dynamic RAM (DRDRAM), and a memory bus dynamic RAM (RDRAM).

What is claimed is:

1. A long short-term memory (LSTM) model-based disease prediction method, comprising:
    obtaining first medical data of a target object and second medical data of an associated object, wherein there is a blood relationship between the target object and the associated object; the first medical data comprises a medication history, a disease history, and a surgery history; the second medical data comprises a genetic disease treatment history;
    inputting the first medical data and the second medical data into a first LSTM network in a trained LSTM model for operation, to obtain a hidden state vector sequence in the first LSTM network, wherein the LSTM model comprises the first LSTM network for encoding and a second LSTM network for decoding;
    inputting the hidden state vector sequence into the second LSTM network for operation, to obtain a disease prediction result, wherein the disease prediction result comprises a predicted disease type and a corresponding incidence rate;
    selecting a predicted disease with an incidence rate higher than a preset threshold from the disease prediction result, and recording the predicted disease as a designated disease, and obtaining, based on a preset disease association network, an associated disease directly connected to the designated disease, wherein network nodes of the association network are different types of diseases; and
    outputting the disease prediction result and the associated disease.

2. The LSTM model-based disease prediction method according to claim 1, wherein the step of inputting the first medical data and the second medical data into a first LSTM network in a trained LSTM model for operation, to obtain a hidden state vector sequence in the first LSTM network comprises:
    dividing the first medical data into multiple data sequences based on preset time periods;
    obtaining a designated impact factor of the genetic disease in the second medical data on other diseases based on a preset correspondence between the genetic disease and impact factors of other diseases; and
    inputting the multiple data sequences and the designated impact factor into the first LSTM network in the trained LSTM model for operation, to obtain the hidden state vector sequence in the first LSTM network.

3. The LSTM model-based disease prediction method according to claim 2, wherein the step of inputting the multiple data sequences and the designated impact factor into the first LSTM network in the trained LSTM model for operation, to obtain the hidden state vector sequence in the first LSTM network comprises:
    obtaining a hidden state vector $h_t$ in the first LSTM network according to the following formula: $h_t = \text{LSTM}_{enc}(x_t, h_{t-1})$, wherein t represents the t-th time period; $h_t$ represents a hidden state vector corresponding to the t-th time period; $h_{t-1}$ represents a hidden state vector corresponding to the (t−1)-th time period; $X_t$ represents input data in the t-th time period; and $\text{LSTM}_{enc}$ refers to an encoding operation using the first LSTM network, wherein $X_t$ comprises first medical data corresponding to the t-th time period and a designated impact factor corresponding to the t-th time period; and
    constructing a hidden state vector sequence $h_1, h_2, \ldots, h_n$ by using hidden state vectors corresponding to multiple preset time periods, wherein there are n time periods in total.

4. The LSTM model-based disease prediction method according to claim 3, wherein the step of constructing a hidden state vector sequence $h_1, h_2, \ldots, h_n$ by using hidden state vectors corresponding to multiple preset time periods, wherein there are n time periods in total, comprises:
    obtaining the final hidden state vector $c_i$ in the first LSTM network according to the following formulas:

$$c_i = \sum_{j=1}^{n} \alpha_{ij} h_j, \; \alpha_{ij} = \frac{\exp(e_{ij})}{\sum_{k=1}^{n} \exp(e_{ik})}, \text{ and } e_{ij} = \text{score}(s_i, h_j),$$

wherein $a_{ij}$ represents a weighting parameter, and there are n time periods in total; $s_i$ represents the i-th hidden state vector in the second LSTM network; $\text{score}(s_i, h_j)$ represents a score calculated based on $s_i$ and $h_j$ using a preset score function; and
    constructing a hidden state vector sequence $c_1, c_2, \ldots, c_n$ by using final hidden state vectors corresponding to multiple preset time periods.

5. The LSTM model-based disease prediction method according to claim 1, wherein the step of inputting the hidden state vector sequence into the second LSTM network for operation, to obtain a disease prediction result, wherein the disease prediction result comprises a predicted disease type and a corresponding incidence rate, comprises:

inputting the hidden state vector sequence into the second LSTM network for operation, to obtain a high-dimensional vector sequence that is output by the second LSTM network; and interpreting the high-dimensional vector sequence based on a preset correspondence between a component vector and a meaning of the prediction result, so as to obtain disease prediction results in different time periods in the future, wherein the disease prediction result comprises the predicted disease type and the corresponding incidence rate.

6. The LSTM model-based disease prediction method according to claim 1, wherein after the step of inputting the hidden state vector sequence into the second LSTM network for operation, to obtain a disease prediction result, wherein the disease prediction result comprises a predicted disease type and a corresponding incidence rate, the method comprises:

receiving multiple input improvement factor groups, and inputting the improvement factor groups, the first medical data, and the second medical data into the trained LSTM model for calculation, wherein the improvement factor groups comprise carrying out of medication or surgery at designated time points;

obtaining multiple groups of improved disease prediction results respectively corresponding to the multiple improvement factor groups output by the LSTM model, wherein the improved disease prediction results comprise predicted disease types and corresponding incidence rates; and selecting a final improved disease prediction result from the multiple groups of improved disease prediction results based on a preset selection rule, and generating a recommended treatment plan, wherein the recommended treatment plan is accompanied by the improvement factor group corresponding to the final improved disease prediction result.

7. The LSTM model-based disease prediction method according to claim 1, wherein the disease association network is a knowledge graph network; before the step of obtaining, based on the preset disease association network, the associated disease directly connected to the designated disease, wherein the network nodes of the association network are different types of diseases, the method comprises:

using a preset knowledge graph construction tool to identify initial entities from designated information collected in advance, wherein the designated information records at least the designated disease, and the initial entities comprise at least the designated disease;

deduplicating the initial entities to obtain final entities; and extracting a relationship between the final entities from the designated information to form a triplet, and generating the knowledge graph network based on the triplet.

8. A computer device, comprising a memory and a processor, wherein the memory stores a computer program, the processor executes the computer program to perform a long short-term memory (LSTM) model-based disease prediction method, and the LSTM model-based disease prediction method comprises:

obtaining first medical data of a target object and second medical data of an associated object, wherein there is a blood relationship between the target object and the associated object; the first medical data comprises a medication history, a disease history, and a surgery history; the second medical data comprises a genetic disease treatment history;

inputting the first medical data and the second medical data into a first LSTM network in a trained LSTM model for operation, to obtain a hidden state vector sequence in the first LSTM network, wherein the LSTM model comprises the first LSTM network for encoding and a second LSTM network for decoding;

inputting the hidden state vector sequence into the second LSTM network for operation, to obtain a disease prediction result, wherein the disease prediction result comprises a predicted disease type and a corresponding incidence rate;

selecting a predicted disease with an incidence rate higher than a preset threshold from the disease prediction result, and recording the predicted disease as a designated disease, and obtaining, based on a preset disease association network, an associated disease directly connected to the designated disease, wherein network nodes of the association network are different types of diseases; and outputting the disease prediction result and the associated disease.

9. The computer device according to claim 8, wherein the step of inputting the first medical data and the second medical data into a first LSTM network in a trained LSTM model for operation, to obtain a hidden state vector sequence in the first LSTM network comprises:

dividing the first medical data into multiple data sequences based on preset time periods;

obtaining a designated impact factor of the genetic disease in the second medical data on other diseases based on a preset correspondence between the genetic disease and impact factors of other diseases; and inputting the multiple data sequences and the designated impact factor into the first LSTM network in the trained LSTM model for operation, to obtain the hidden state vector sequence in the first LSTM network.

10. The computer device according to claim 9, wherein the step of inputting the multiple data sequences and the designated impact factor into the first LSTM network in the trained LSTM model for operation, to obtain the hidden state vector sequence in the first LSTM network comprises:

obtaining a hidden state vector $h_t$ in the first LSTM network according to the following formula: $h_t = \text{LSTM}_{enc}(x_t, h_{t-1})$, wherein t represents the t-th time period; $h_t$ represents a hidden state vector corresponding to the t-th time period; $h_{t-1}$ represents a hidden state vector corresponding to the (t−1)-th time period; $X_t$ represents input data in the t-th time period; and $\text{LSTM}_{enc}$ refers to an encoding operation using the first LSTM network, wherein $X_t$ comprises first medical data corresponding to the t-th time period and a designated impact factor corresponding to the t-th time period; and constructing a hidden state vector sequence $h_1, h_2, \ldots, h_n$ by using hidden state vectors corresponding to multiple preset time periods, wherein there are n time periods in total.

11. The computer device according to claim 10, wherein the step of constructing a hidden state vector sequence $h_1, h_2, \ldots, h_n$ by using hidden state vectors corresponding to multiple preset time periods, wherein there are n time periods in total, comprises:

obtaining the final hidden state vector $c_i$ in the first LSTM network according to the following formulas:

$$c_i = \sum_{j=1}^{n} \alpha_{ij} h_j, \; \alpha_{ij} = \frac{\exp(e_{ij})}{\sum_{k=1}^{n} \exp(e_{ik})}, \text{ and } e_{ij} = \text{score}(s_i, h_j),$$

wherein $a_{ij}$ represents a weighting parameter, and there are n time periods in total; $s_i$ represents the i-th hidden state vector in the second LSTM network; score($s_i$,$h_j$) represents a score calculated based on $s_i$ and $h_j$ using a preset score function; and constructing a hidden state vector sequence $c_1, c_2, \ldots, c_n$ by using final hidden state vectors corresponding to multiple preset time periods.

12. The computer device according to claim 8, wherein the step of inputting the hidden state vector sequence into the second LSTM network for operation, to obtain a disease prediction result, wherein the disease prediction result comprises a predicted disease type and a corresponding incidence rate, comprises:

inputting the hidden state vector sequence into the second LSTM network for operation, to obtain a high-dimensional vector sequence that is output by the second LSTM network; and interpreting the high-dimensional vector sequence based on a preset correspondence between a component vector and a meaning of the prediction result, so as to obtain disease prediction results in different time periods in the future, wherein the disease prediction result comprises the predicted disease type and the corresponding incidence rate.

13. The computer device according to claim 8, wherein after the step of inputting the hidden state vector sequence into the second LSTM network for operation, to obtain a disease prediction result, wherein the disease prediction result comprises a predicted disease type and a corresponding incidence rate, the method comprises:

receiving multiple input improvement factor groups, and inputting the improvement factor groups, the first medical data, and the second medical data into the trained LSTM model for calculation, wherein the improvement factor groups comprise carrying out of medication or surgery at designated time points;

obtaining multiple groups of improved disease prediction results respectively corresponding to the multiple improvement factor groups output by the LSTM model, wherein the improved disease prediction results comprise predicted disease types and corresponding incidence rates; and selecting a final improved disease prediction result from the multiple groups of improved disease prediction results based on a preset selection rule, and generating a recommended treatment plan, wherein the recommended treatment plan is accompanied by the improvement factor group corresponding to the final improved disease prediction result.

14. The computer device according to claim 8, wherein the disease association network is a knowledge graph network; before the step of obtaining, based on the preset disease association network, the associated disease directly connected to the designated disease, wherein the network nodes of the association network are different types of diseases, the method comprises:

using a preset knowledge graph construction tool to identify initial entities from designated information collected in advance, wherein the designated information records at least the designated disease, and the initial entities comprise at least the designated disease;

deduplicating the initial entities to obtain final entities; and extracting a relationship between the final entities from the designated information to form a triplet, and generating the knowledge graph network based on the triplet.

15. A non-transitory computer readable storage medium, wherein the computer readable storage medium stores a computer program, the computer program is executed by a processor to perform a long short-term memory (LSTM) model-based disease prediction method, and the LSTM model-based disease prediction method comprises:

obtaining first medical data of a target object and second medical data of an associated object, wherein there is a blood relationship between the target object and the associated object; the first medical data comprises a medication history, a disease history, and a surgery history; the second medical data comprises a genetic disease treatment history;

inputting the first medical data and the second medical data into a first LSTM network in a trained LSTM model for operation, to obtain a hidden state vector sequence in the first LSTM network, wherein the LSTM model comprises the first LSTM network for encoding and a second LSTM network for decoding;

inputting the hidden state vector sequence into the second LSTM network for operation, to obtain a disease prediction result, wherein the disease prediction result comprises a predicted disease type and a corresponding incidence rate;

selecting a predicted disease with an incidence rate higher than a preset threshold from the disease prediction result, and recording the predicted disease as a designated disease, and obtaining, based on a preset disease association network, an associated disease directly connected to the designated disease, wherein network nodes of the association network are different types of diseases; and outputting the disease prediction result and the associated disease.

16. The non-transitory computer readable storage medium according to claim 15, wherein the step of inputting the first medical data and the second medical data into a first LSTM network in a trained LSTM model for operation, to obtain a hidden state vector sequence in the first LSTM network comprises:

dividing the first medical data into multiple data sequences based on preset time periods;

obtaining a designated impact factor of the genetic disease in the second medical data on other diseases based on a preset correspondence between the genetic disease and impact factors of other diseases; and inputting the multiple data sequences and the designated impact factor into the first LSTM network in the trained LSTM model for operation, to obtain the hidden state vector sequence in the first LSTM network.

17. The non-transitory computer readable storage medium according to claim 16, wherein the step of inputting the multiple data sequences and the designated impact factor into the first LSTM network in the trained LSTM model for operation, to obtain the hidden state vector sequence in the first LSTM network comprises:

obtaining a hidden state vector $h_t$ in the first LSTM network according to the following formula: $h_t = \text{LSTM}_{enc}(x_t, h_{t-1})$, wherein t represents the t-th time period; $h_t$ represents a hidden state vector corresponding to the t-th time period; $h_{t-1}$ represents a hidden state vector corresponding to the (t−1)-th time period; $X_t$ represents input data in the t-th time period; and $LSTM_{enc}$ refers to an encoding operation using the first LSTM network, wherein $X_t$ comprises first medical data corresponding to the t-th time period and a designated impact factor corresponding to the t-th time period; and constructing a hidden state vector sequence $h_1, h_2, \ldots, h_n$ by using hidden state vectors corresponding to multiple preset time periods, wherein there are n time periods in total.

18. The non-transitory computer readable storage medium according to claim 17, wherein the step of constructing a hidden state vector sequence $h_1, h_2, \ldots, h_n$ by using hidden state vectors corresponding to multiple preset time periods, wherein there are n time periods in total, comprises:

obtaining the final hidden state vector $c_i$ in the first LSTM network according to the following formulas:

$$c_i = \sum_{j=1}^{n} \alpha_{ij} h_j, \ \alpha_{ij} = \frac{\exp(e_{ij})}{\sum_{k=1}^{n} \exp(e_{ik})}, \text{ and } e_{ij} = \text{score}(s_i, h_j),$$

wherein $a_{ij}$ represents a weighting parameter, and there are n time periods in total; $s_i$ represents the i-th hidden state vector in the second LSTM network; $\text{score}(s_i, h_j)$ represents a score calculated based on $s_i$ and $h_j$ using a preset score function; and constructing a hidden state vector sequence $c_1, c_2, \ldots, c_n$ by using final hidden state vectors corresponding to multiple preset time periods.

19. The non-transitory computer readable storage medium according to claim 15, wherein the step of inputting the hidden state vector sequence into the second LSTM network for operation, to obtain a disease prediction result, wherein the disease prediction result comprises a predicted disease type and a corresponding incidence rate, comprises:

inputting the hidden state vector sequence into the second LSTM network for operation, to obtain a high-dimensional vector sequence that is output by the second LSTM network; and interpreting the high-dimensional vector sequence based on a preset correspondence between a component vector and a meaning of the prediction result, so as to obtain disease prediction results in different time periods in the future, wherein the disease prediction result comprises the predicted disease type and the corresponding incidence rate.

20. The non-transitory computer readable storage medium according to claim 15, wherein after the step of inputting the hidden state vector sequence into the second LSTM network for operation, to obtain a disease prediction result, wherein the disease prediction result comprises a predicted disease type and a corresponding incidence rate, the method comprises:

receiving multiple input improvement factor groups, and inputting the improvement factor groups, the first medical data, and the second medical data into the trained LSTM model for calculation, wherein the improvement factor groups comprise carrying out of medication or surgery at designated time points;

obtaining multiple groups of improved disease prediction results respectively corresponding to the multiple improvement factor groups output by the LSTM model, wherein the improved disease prediction results comprise predicted disease types and corresponding incidence rates; and selecting a final improved disease prediction result from the multiple groups of improved disease prediction results based on a preset selection rule, and generating a recommended treatment plan, wherein the recommended treatment plan is accompanied by the improvement factor group corresponding to the final improved disease prediction result.

\* \* \* \* \*